(12) United States Patent  
Lombardo

(10) Patent No.: US 6,540,748 B2
(45) Date of Patent: Apr. 1, 2003

(54) SURGICAL SCREW SYSTEM AND METHOD OF USE

(75) Inventor: Alan Lombardo, Kinnelon, NJ (US)

(73) Assignee: Blackstone Medical, Inc., Springfield, MA (US)

( * ) Notice: Subject to any disclaimer, the term of this patent is extended or adjusted under 35 U.S.C. 154(b) by 338 days.

(21) Appl. No.: 09/751,099

(22) Filed: Dec. 28, 2000

(65) Prior Publication Data

US 2001/0001119 A1 May 10, 2001

Related U.S. Application Data

(63) Continuation of application No. 09/407,044, filed on Sep. 27, 1999, now abandoned.

(51) Int. Cl.[7] .............................................. A61B 17/70
(52) U.S. Cl. .......................................... 606/61; 606/73
(58) Field of Search .............................. 606/61, 60, 73, 606/72, 53

(56) References Cited

U.S. PATENT DOCUMENTS

| 5,005,562 A | | 4/1991 | Cotrel |
| 5,209,751 A | | 5/1993 | Farris et al. |
| 5,545,165 A | | 8/1996 | Biedermann et al. |
| 5,584,831 A | | 12/1996 | McKay |
| 5,667,508 A | | 9/1997 | Errico et al. |
| 5,716,355 A | | 2/1998 | Jackson et al. |
| 5,733,286 A | | 3/1998 | Errico et al. |
| 5,752,957 A | | 5/1998 | Ralph et al. |
| 5,810,818 A | | 9/1998 | Errico et al. |
| 5,882,350 A | * | 3/1999 | Ralph et al. .................... 606/61 |
| 5,885,286 A | * | 3/1999 | Sherman et al. ............... 606/61 |
| 5,899,905 A | | 5/1999 | Errico et al. |
| 6,010,503 A | * | 1/2000 | Richelsoph et al. .......... 606/61 |
| 6,022,350 A | | 2/2000 | Ganem |
| 6,053,917 A | * | 4/2000 | Sheman et al. ................ 606/61 |
| 6,063,090 A | * | 5/2000 | Schlapfer ...................... 606/61 |
| 6,074,391 A | * | 6/2000 | Metz-Stavenhagen et al. ... 606/61 |
| 6,077,262 A | * | 6/2000 | Schlapfer et al. ............. 606/61 |

FOREIGN PATENT DOCUMENTS

EP            625337 A1  * 11/1994  .................. 606/61

* cited by examiner

Primary Examiner—Jeffrey A. Smith
(74) Attorney, Agent, or Firm—Dreier & Baritz LLP

(57) ABSTRACT

A surgical screw system for use with implantation rods includes a screw member, a receiver member, a pressure cap and a locking device. The screw member has a shaft and a head with a spherical undersurface and a conical tapered recess. The receiver member has an upper and lower portion, a u-shaped rod receiving channel and an axial bore. The u-shaped channel has two lateral legs at the upper portion and forms an opening leading to the axial bore. The axial bore near the lower portion includes an inwardly conical tapered surface which has a diameter larger than the shaft of the screw member but smaller than the head of the screw member. The conical surface forms a support upon which the spherical undersurface of the head of the screw member rests when the screw member is guided through the bore of the lower portion of the receiver member. The pressure cap is positioned within the axial bore and situated upon the head of the screw member. The locking device is designed for securing the rod within the u-shaped channel of the receiver member by applying a tightening torque upon the rod when positioned within the opening and the bore near the upper portion of the receiver member.

30 Claims, 4 Drawing Sheets

SURGICAL SCREW SYSTEM AND METHOD OF USE

CROSS-REFERENCE TO RELATED APPLICATIONS

This application is a continuation of application Ser. No. 09/407,044, filed Sep. 27, 1999, and now abandoned.

BACKGROUND OF THE INVENTION

The present invention relates to a surgical screw system for use with implantation rods, and related methods of using a surgical screw system with implantation rods.

The bones and connective tissue of an adult human spinal column consists of more than 20 discrete bones coupled sequentially to one another by a tri-joint complex. The complex consists of an anterior disc and two posterior facet joints. The anterior discs of adjacent bones are cushioned by cartilage spacers referred to as intervertebral discs. The over 20 bones of the spinal column are anatomically categorized as one of four classification: cervical, thoracic, lumbar, or sacral. The cervical portion of the spine which comprises the top of the spine up to the base of the skull, includes the first 7 vertebrae. The intermediate 12 bones are thoracic vertebrae, and connect to the lower spine comprising the 5 lumbar vertebrae. The base of the spine is a sacral bones (including the coccyx).

The spinal column of bones is high complex in that it includes the over 20 bones coupled to one another, housing and protecting critical elements of the nervous system having innumerable peripheral nerves and circulatory bodies in close proximity. Despite its complexity, the spine is a highly flexible structure, capable of a high degree of curvature and twist in nearly every direction.

Genetic or developmental irregularities, trauma, chronic stress, tumors and disease, however, can result in spinal pathologies which either limit this range of motion, or which threatens the critical elements of the nervous system housed within the spinal column. A variety of systems have been disclosed in the art which achieve this immobilization by implanting artificial assemblies in or on the spinal column. These assemblies may be classified as anterior posterior or lateral implants. Lateral and anterior assemblies are coupled to the anterior portion of the spine which is in the sequence of vertebral bodies. Posterior implants generally comprise pairs of rods, which are aligned along the axis which the bones are to be disposed, and which are then attached to the spinal column by either hooks which couple to the lamina or attach to the transverse processes, or by screws which are inserted through the pedicles.

It is desirable, during surgical implantation of such orthopedic devices, to have a multi-axial screw system that provides a consistent lock as well as reliability, durability, and ease of installment.

SUMMARY OF THE INVENTION

The present invention relates to a surgical screw system for use with implantation rods. In one embodiment, the system comprises a screw member, a receiver member, a pressure cap and a locking device. The screw member has a head and shaft; the head of the screw member has a spherical undersurface and a conical tapered recess. The receiver member has upper and lower portions, a u-shaped receiving channel and an axial bore. The u-shaped channel has two lateral legs at the upper portion of the receiver member and forms an opening leading to the axial bore; the conical surface has a diameter larger than the shaft of the screw member and a diameter smaller than the head of the screw member. The conical surface forms a support upon which the spherical undersurface of the head of the screw member rests when the screw member is guided through the bore to the lower portion of the receiver member. The pressure cap of the system is positioned within the axial bore of the receiver member and is situated upon the head of the screw member; the pressure cap has upper and lower portions and the upper portion of the cap comprises a concave radial portion upon which the rod is positioned, and the lower portion comprises a spherical portion positioned upon the conical tapered recess of the head of the screw member. The locking device is designed for securing the rod within the u-shaped channel of the receiver member by applying a tightening torque upon the rod when positioned within the opening and the bore near the upper portion of the receiver member.

In another embodiment, the undersurface of the head and the shaft of the screw member comprise threaded portions. In still another embodiment, the legs of the u-shaped channel has internal threads and the threads may be buttress threads.

In a further embodiment, the conical tapered recess of the head of the screw member comprises an aperture coaxial to the shaft and designed to engage a fastening device. The pressure cap further comprises an axial bore extending from the upper through lower ends of the cap; the bore of the pressure cap corresponds to the aperture of the head of the screw member allowing an access for the fastening device.

In still a further embodiment, the receiver member further comprises a rectangular key-locking segment and a cylindrical undercut situated adjacent to the bore. In yet a further embodiment, the pressure cap further comprises a cylindrical undercut and a retaining ring; the key-locking segment and the undercut of the receiver member are designed to engage the undercut and the ring of the pressure cap to form an anti-rotation and locking mechanism.

In yet another embodiment, the legs of the u-shaped channel of the receiver member further comprises a threaded portion and the locking device further comprises a corresponding threaded portion. In another embodiment, the threaded portions are buttress threads. In yet another embodiment, the locking device is a set screw. In still another embodiment, the locking device is a top locking nut. In still yet another embodiment, the aperture of the head of the screw member is hexagon-shaped and the fastening device is a hexagon socket screw key.

In another embodiment, the axial bore of the receiver member comprises a plurality of slots descending down the legs of the u-shaped channel and the locking device comprises at least one protrusion designed to engage at least one of the slots on the legs of the u-shaped channel of the receiver member to secure the locking device within the receiver member. In a further embodiment, the locking device comprises a top and bottom portion; the bottom portion has a convex recess designed for contacting the curvature of the rod. In still a further embodiment, the screw member, receiver member and the pressure cap may be factory set. The operating physician just needs to attach the screw member to a bone, place the implantation rod into the receiver member and secure the rod into the receiver member using the locking device.

In another embodiment, the present invention relates to a surgical screw and rod implantation system, comprising at least one rod and at least one surgical screw apparatus. The apparatus comprises a screw member having a head and a shaft, the head of the screw member has a spherical undersurface and a conical tapered recess; a receiver member has upper and lower portions, a u-shaped rod receiving channel, and an axial bore; the u-shaped channel has two lateral legs at the upper portion of the receiver member and forms an opening leading to the axial bore; the axial bore near the lower portion of the receiver member includes an inwardly conical tapered surface, the conical tapered surface has a diameter larger than the shaft of the screw member and a diameter smaller than the head of the screw member thereby forming a support upon which the spherical undersurface of the head of the screw member rests when the screw member is guided through the bore to the lower portion of the receiver member; a pressure cap positioned within the axial bore of the receiver member and situated upon the head of the screw member; the pressure cap having upper and lower ends, the upper end of the cap comprising a concave radial portion upon which the rod is positioned, the lower end comprising a spherical portion situated upon the conical tapered recess of the head of the screw member; and a locking device for securing the rod within the u-shaped channel of the receiver member by applying a tightening torque upon the rod when positioned within the opening and the bore near the upper portion of the receiver member.

In still another embodiment, the undersurface of the head and the shaft of the screw member comprise threaded portions. In yet another embodiment, the conical tapered recess of the head of the screw member comprises an aperture coaxial to the shaft and designed to engage a fastening device. The pressure cap further comprises an axial bore extending from the upper through the lower ends of the aperture of the head of the screw member allowing access for the fastening device.

In a further embodiment, the receiver member further comprises a rectangular key-locking segment and a cylindrical undercut situated adjacent to the bore; the pressure cap further comprises a cylindrical undercut and a retaining ring. In still a further embodiment, the key-locking segment and the undercut of the receiver member are designed to engage the undercut and the ring of the cap to form an anti-rotation and locking mechanism.

In yet a further embodiment, the axial bore of the receiver member further comprises a threaded portion and the locking device further comprises a corresponding threaded portion.

In still yet a further embodiment, the axial bore of the receiver member comprises a plurality of slots descending down the legs of the u-shaped channel and the locking device comprising at least one protrusion designed to engage at least one of the slots of the receiver member to secure the locking device within the receiver member. In another further embodiment, the locking device comprises a top and bottom portion; the bottom portion has a convex recess designed for contacting the curvature of the rod.

In another embodiment, the present invention relates to a method of using a surgical screw system with an implantation rod. The method comprises: providing a screw member, a receiver member and a pressure cap; the screw member having a head and a shaft, the head of the screw member having a spherical undersurface and a conical tapered recess; the receiver member has an upper and lower portion, a u-shaped rod receiving channel and an axial bore; the u-shaped rod receiving channel has two lateral legs at the upper portion of the receiver member and forms an opening leading to the axial bore; the axial bore near the lower portion of the receiver member including an inwardly conical tapered surface; the conical surface has a diameter larger than the shaft of the screw member and a diameter smaller than the head of the screw member; the pressure cap has upper and lower ends, the upper end comprising a concave radial portion and the lower end comprising a spherical portion; inserting the screw member into the bore of the receiver member and positioning the screw member toward the lower portion of the receiver member such that the conical surface of the bore forms a support upon which the spherical undersurface of the head of the screw member rests upon the conical surface and the shaft of the screw member extends from the receiver member; inserting the pressure cap into the bore of the receiver member and positioning the spherical portion of the cap upon the conical tapered recess of the head of the screw member, and aligning the concave radial portion of the cap with the u-shaped channel such that the concave radial portion is to ready to receive the rod; securing the screw member into the spinal column of the patient; positioning the rod upon the concave radial portion of the cap; and securing the rod within the u-shaped channel of the receiver member using a locking device; the locking device being positioned within the opening and the bore near the upper portion of the receiver member.

In a further embodiment, the head and the shaft of the screw member comprise threaded portions. In still a further embodiment, the conical tapered recess of the head of the screw member comprises an aperture coaxial to the shaft and designed to engage a fastening device; the cap further comprises an axial bore extending from the upper through lower end of the cap, the bore of the cap corresponding to the aperture of the head of the screw member allowing access for the fastening device.

In still a further embodiment, the screw member is screwed into a spinal column using a fastening device and in another embodiment, the fastening device is a hexagon socket screw key.

In yet a further embodiment, the pressure cap is locked within the bore of the receiver member prior to the screw member being screwed into the spinal column. In still yet a further embodiment, the receiver member further comprises a rectangular key-locking segment and a cylindrical undercut situated adjacent to the bore; the pressure cap furthers comprising a cylindrical undercut and a retaining ring; the key-locking segment and the undercut of the receiver member being designed to engage the undercut and the ring of the cap to form an anti-rotation and locking mechanism.

In another embodiment, the legs of the u-shaped channel of the receiver member further comprise a threaded portion and the locking-device further comprises a corresponding threaded portion. In still another embodiment, the locking device is a set screw and in another embodiment, the locking device is a top locking nut.

In yet another embodiment, the axial bore of the receiver member comprises a plurality of slots descending down the legs of the u-shaped channel and the locking device comprises at least one protrusion designed to engage at least one of the slots of the legs of the u-shaped channel of the receiver member to secure the locking device with the receiver member.

In a further embodiment, the locking device comprises a top and bottom portion; the bottom portion having a convex recess designed for contacting the curvature of the rod. In still a further embodiment, the convex recess of the locking device is aligned with the curvature of the rod before locking the locking device within the receiver member.

BRIEF DESCRIPTION OF THE DRAWINGS:

A more complete appreciation of the present invention and many of the attendant advantages thereof will be readily understood by reference to the following description when considered in connection with the accompanying drawings in which.

Among those benefits and improvements that have been disclosed, other objects and advantages of this invention will become apparent from the following description taken in conjunction with the accompanying drawings. The drawings constitute a part of this specification and include exemplary embodiments of the present invention and illustrate various objects and features thereof.

DETAIL DESCRIPTION OF THE INVENTION

Figure 1:
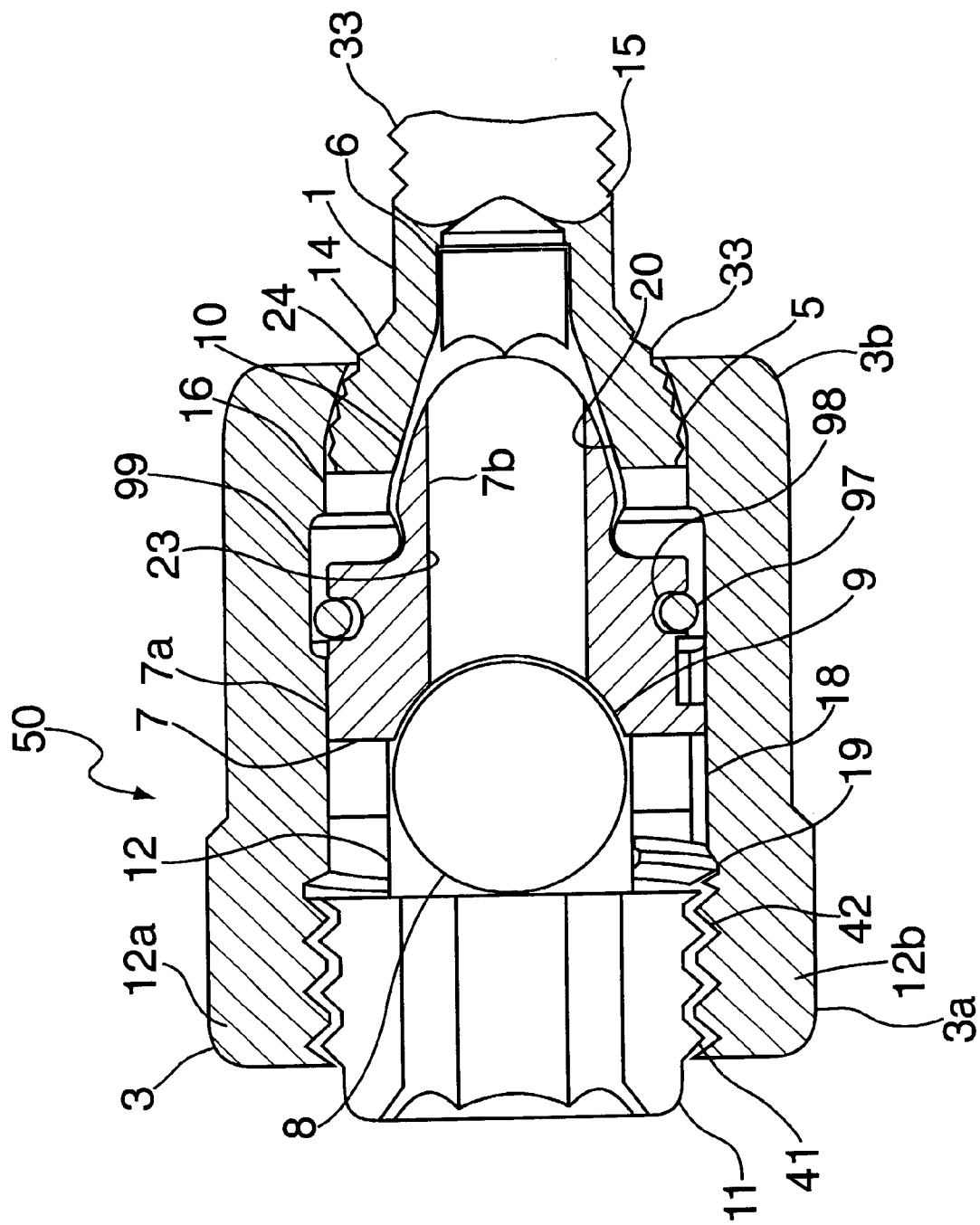
FIG. 1 is a cross sectional view of the surgical screw system of the present invention.

Referring now to the drawings wherein like reference numerals designate identical or corresponding parts throughout the several views, and more particularly to FIG. 1 wherein the surgical screw system 50 of the present invention is illustrated. The surgical screw system 50 comprises a screw member 1 having a head 14 and shaft 15. The head 14 has spherical undersurface 24 and a conical tapered recess 10. The system 50 further comprises a receiver member 3 having upper and lower portions, 3a and 3b respectively, a u-shaped rod receiving channel 12, and an axial bore 16. The u-shaped channel 12 has two lateral legs, 12a and 12b respectively, at the upper portion 3a of the receiver member 3 and forms an opening leading to the axial bore 16. The axial bore 16 near the lower portion 3b of the receiver member 3 includes an inwardly conical tapered surface 5. The conical surface 5 has a diameter larger than the shaft 15 of the screw member 1 and a diameter smaller than the head 14 of the screw member 1. The conical surface 5 forms a support upon which the spherical undersurface 24 of the head 14 rests when the when the screw member 1 is guided through the bore 16 to the lower portion 3b of the receiver member 3. The system 50 also comprises a pressure cap 7 which is positioned with the axial bore 16 of the receiver member 3 and situated upon the head 14 of the screw member 1. The pressure cap 7 has upper and lower ends, 7a and 7b respectively; the upper end 7a of the pressure cap 7 comprises a concave radial portion 9 upon which a rod 8 is positioned, and the lower end 7b of the pressure cap 7 comprises a spherical portion 20 situated upon the conical tapered recess 10 of the head 14 of the screw member 1. The system 50 further comprises a locking device 11 for securing the rod 8 within the u-shaped channel 12 of the receiver member 3 by applying a tightening torque upon the rod 8 when positioned within the opening and bore 16 near the upper portion of 3a of the receiver member 3.

The undersurface 24 of the head 14 and the shaft 15 of the screw member 1 can comprise threaded portions 33. The conical tapered recess 10 of the screw member 1 comprises an aperture 6 coaxial to the shaft 15 and designed to engage a fastening device. The pressure cap 7 further comprises a axial bore 23 extending from the upper end 7a to the lower end 7a of the pressure cap 7. The bore 23 of the pressure cap 7 corresponds to the aperture 6 of the head 14 of the screw member 1 allowing access for the fastening device.

The receiver member 3 also further comprises a rectangular key-locking segment 18 and a cylindrical undercut 99 situated adjacent to the bore 16. The pressure cap 7 further comprises a cylindrical undercut 98 and a retaining ring 97. The key-locking segment 18 and the undercut 99 of the receiver member 3 are designed to engage the undercut 98 and the ring 97 of the pressure cap 7 to form an anti-rotation and locking mechanism.

The axial bore 16 of the receiver member 3 further comprises threaded portions 42 and the locking device comprises corresponding threaded portions 41. The head 14 of the screw member 1 is hexagon-shaped and the fastening device is a hexagon socket screw key.

The locking mechanism of the present invention provides a more consistent locking system. The convex spherical/concave conical taper interface of the present invention occurs at two instances: (a) the spherical undersurface 24 of the head 14 of the screw member 1 and the conical tapered recess surface 5 of the receiver member 3 and (b) the spherical portion 20 of the pressure cap 7 and the conical tapered recess 10 of the head 14 of the screw member 1. The convex spherical/concave conical taper interface at each junction of the locking mechanism of the present invention are wedge jointly. This wedge joint is achieved when a changing force is applied and the convex spherical feature is compressed into the concave conical taper feature. At the periphery point contacts and at the component interfaces, a resultant hoop stress is created. This hoop stress has a wedging effect at the component interfaces, thereby consistently locking the device in position. In addition to the wedging effect, the present invention also provides a mechanical leverage. The wedging effect and mechanical leverage provides for a consistently robust locking mechanism. The consistency is based upon the reproducible nature of the tapered nest geometry. Even when considering tolerance, the taper lock wedging effect and leverage position will always be consistently achieved. If any tolerance variation is encountered, this will translate into a slight variation of height in the longitudinal axis of the assembly which is negligible as to the function of the locking mechanism and the final device assembly.

Figure 2:
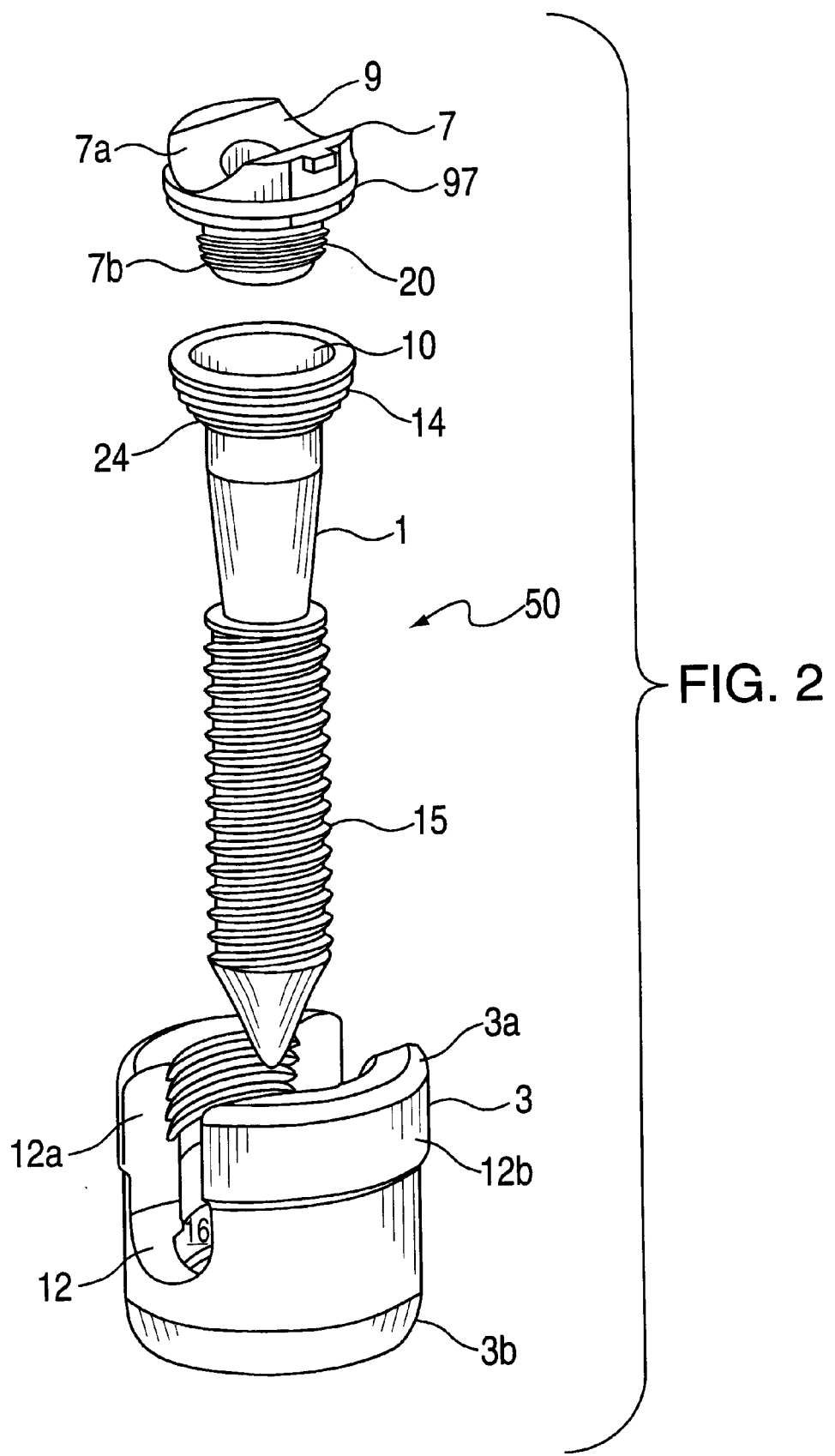
FIG. 2 is a perspective view of the components of the surgical screw system.

FIG. 2 depicts a perspective view of the components of the surgical screw system 50 of the present invention. The system 50 comprises a screw member 1, a receiver member 3, a pressure cap 7 and a locking device. The screw member 1 comprises a head 14 and a shaft 15. The head 14 includes a spherical undersurface 24 and a conical tapered recess 10. FIG. 2 depicts the screw member 1 prior to insertion into the axial bore 16 of the receiver member 3. The receiver member 3 has upper and lower portions, 3a and 3b, a u-shaped channel 12 with two lateral legs 12a and 12b, and an axial bore. The pressure cap 7 comprises upper and lower ends, 7a and 7b respectively; the upper end 7a of the pressure cap 7 comprises a concave radial portion 9 and the lower end 7b comprises a spherical portion 20. The pressure cap also has a retaining ring 97.

Figure 3:
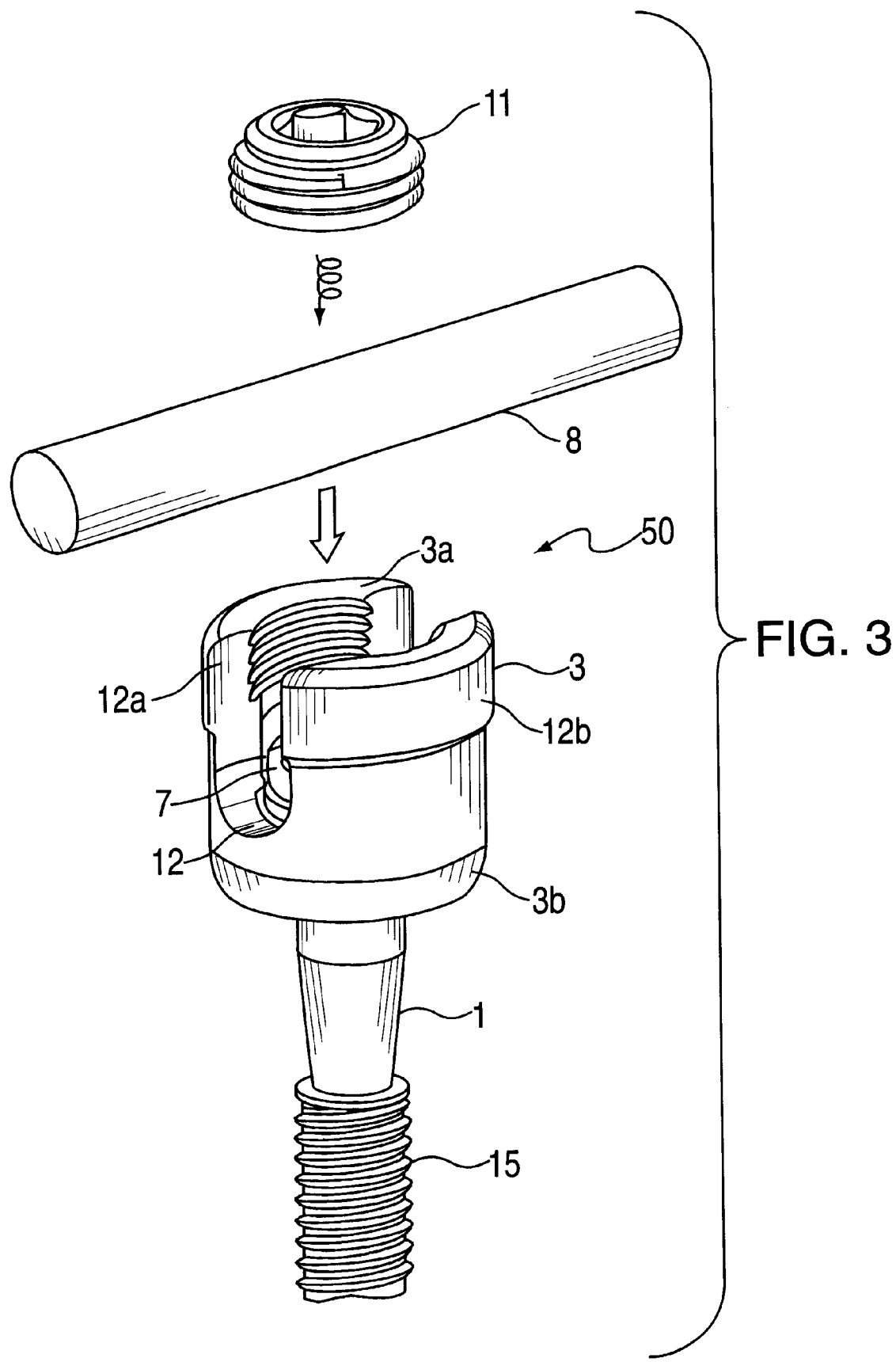
FIG. 3 is a perspective view of the surgical screw system and the rod unassembled.

FIG. 3 depicts the system 50 of the present invention in relation to an implantation rod 8 prior to assembly. The rod 8 is inserted into u-shaped channel 12 and within the bore 16 of the receiver member 3. The channel 12 has legs, 12a and 12b, that support the rod 8 upon insertion. The rod 8 is situated upon the concave radial portion 9 of pressure cap 7. The locking device 11 is secured upon the rod 8 and within the opening and bore 16 near the upper portion 3a of the receiver member 3.

Figure 4:
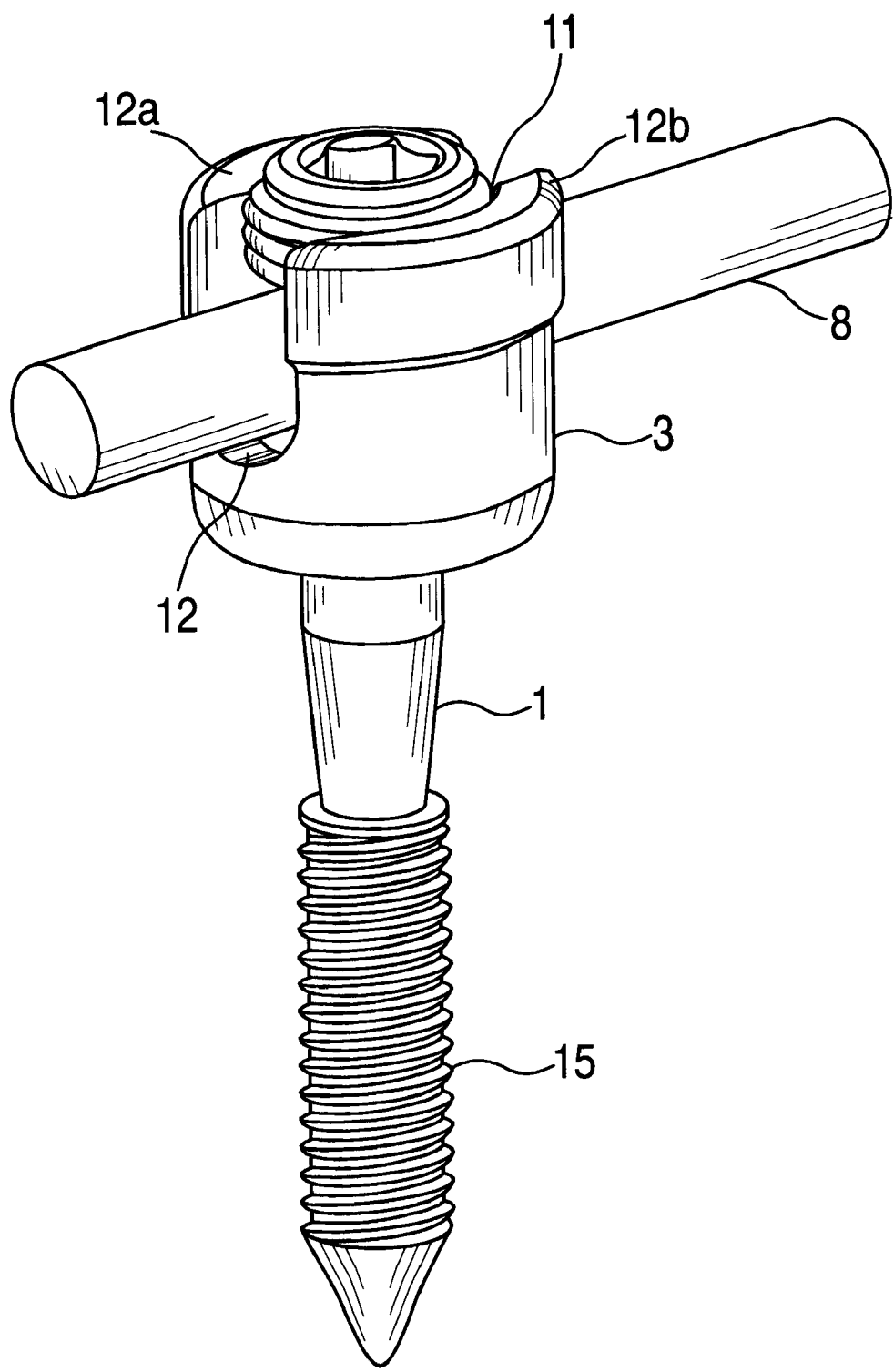
FIG. 4 is a perspective view of the surgical screw system and the rod assembled.

FIG. 4 illustrates the system 50 in assembled form. The rod 8 sits within the channel 12 and bore 16 and is supported by the legs 12a and 12b. The locking device 11 is used to secure the rod 8 within the channel 12 and bore 16 by applying a tightening torque upon the rod 8. The shaft 15 of the screw member 1 dangles from the receiver member 3 and allows for a two dimensional adjustment and multi-axial capabilities.

Numerous modifications and variations of the present invention are possible in light of the above teachings. It is therefore to be understood that within the scope of the attendant claims appended thereto, this invention may be practiced otherwise than as specifically disclosed herein.

What is claimed is:

1. A surgical screw system for use with implantation rods, comprising:
    a screw member having a head and a shaft, said head of said screw member having a spherical undersurface and a conical tapered recess;
    a receiver member having upper and lower portions, a u-shaped rod receiving channel, and an axial bore; said u-shaped channel having two lateral legs at said upper portion of said receiver member and forming an opening leading to said axial bore; said axial bore near said lower portion of said receiver member including an inwardly conical tapered surface, said conical surface having a diameter larger than said shaft of said screw member and a diameter smaller than said head of said screw member; said conical surface forming a support upon which said spherical undersurface of said head of said screw member rests when said screw member is guided through said bore to said lower portion of said receiver member;
    a pressure cap positioned within said axial bore of said receiver member and situated upon said head of said screw member; said pressure cap having upper and lower ends, said upper end of said cap comprising a concave radial portion upon which the rod is positioned, said lower end comprising a spherical portion situated upon said conical tapered recess of said head of said screw member; and
    a locking device for securing the rod within said u-shaped channel of said receiver member by applying a tightening torque upon the rod when positioned within said opening and said bore near said upper portion of said receiver member.

2. The system of claim 1 wherein said undersurface of said head and said shaft of said screw member comprise threaded portions.

3. The system of claim 1 wherein said conical tapered recess of said head of said screw member comprising an aperture coaxial to said shaft and designed to engage a fastening device; said pressure cap further comprising an axial bore extending from said upper through said lower ends of said cap; said bore of said cap corresponding to said aperture of said head of said screw member allowing an access for said fastening device.

4. The system of claim 3 wherein said aperture of said head of said screw member is hexagon shaped and said fastening device is a hexagon socket screw key.

5. The system of claim 1 wherein said legs of said u-shaped channel of said receiver member further comprises a threaded portion and said locking device further comprises a corresponding threaded portion.

6. The system of claim 5 wherein said locking device is a set screw.

7. The system of claim 5 wherein said locking device is a top locking nut.

8. The system of claim 1 wherein said receiver member further comprising a rectangular key-locking segment and a cylindrical undercut situated adjacent to said bore; said pressure cap further comprising a cylindrical undercut and a retaining ring; said key-locking segment and said undercut of said receiver member being designed to engage said undercut and said ring of said cap to form an anti-rotation and locking mechanism.

9. The system of claim 1 wherein said legs of said u-shaped channel of said receiver member comprises a plurality of slots descending down said bore and said locking device comprising at least one protrusion designed to engage at least one of said slots of said legs of said u-shaped channel of said receiver member to secure said locking device within said receiver member.

10. The system of claim 1 wherein said locking device comprises a top and bottom portion, said bottom portion having a convex recess designed for contacting the curvature of the rod.

11. A surgical screw and rod implantation system comprising:
    at least one rod;
    at least one surgical screw apparatus comprising:
        a screw member having a head and a shaft, said head of said screw member having a spherical undersurface and a conical tapered recess;
        a receiver member having upper and lower portions, a u-shaped rod receiving channel, and an axial bore; said u-shaped channel having two lateral legs at said upper portion of said receiver member and forming an opening leading to said axial bore; said axial bore near said lower portion of said receiver member including an inwardly conical tapered surface, said conical tapered surface having a diameter larger than said shaft of said screw member and a diameter smaller than said head of said screw member thereby forming a support upon which said spherical undersurface of said head of said screw member rests when said screw member is guided through said bore to said lower portion of said receiver member;
        a pressure cap positioned within said axial bore of said receiver member and situated upon said head of said screw member; said pressure cap having upper and lower ends, said upper end of said cap comprising a concave radial portion upon which the rod is positioned, said lower end comprising a spherical portion situated upon said conical tapered recess of said head of said screw member; and
        a locking device for securing the rod within said u-shaped channel of said receiver member by applying a tightening torque upon the rod when positioned within said opening and said bore near said upper portion of said receiver member.

12. The system of claim 11 wherein said undersurface of said head and said shaft of said screw member comprise threaded portions.

13. The system of claim 11 wherein said conical tapered recess of said head of said screw member comprising an aperture coaxial to said shaft and designed to engage a fastening device; said pressure cap further comprising an axial bore extending from said upper through said lower ends of said cap; said bore of said cap corresponding to said aperture of said head of said screw member allowing an access for the fastening device.

14. The system of claim 11 wherein said receiver member further comprising a rectangular key-locking segment and a cylindrical undercut situated adjacent to said bore; said pressure cap further comprising a cylindrical undercut and a retaining ring; said key-locking segment and said undercut of said receiver member being designed to engage said undercut and said ring of said cap to form an anti-rotation and locking mechanism.

15. The system of claim 11 wherein said axial bore of said receiver member further comprises a threaded portion and said locking device further comprises a corresponding threaded portion.

16. The system of claim 11 wherein said legs of said u-shaped channel of said receiver member comprises a plurality of slots descending down said bore and said locking device comprising at least one protrusion designed to engage at least one of said slots of said legs of said u-shaped channel of said receiver member to secure said locking device within said receiver member.

17. The system of claim 11 wherein said locking device comprises a top and bottom portion, said bottom portion having a convex recess designed for contacting the curvature of the rod.

18. A method of using a surgical screw system with an implantation rod, said method comprising:

providing a screw member, a receiver member and a pressure cap; said screw member having a head and a shaft, said head of said screw member having a spherical undersurface and a conical tapered recess; said receiver member having upper and lower portions, a u-shaped rod receiving channel and an axial bore; said u-shaped rod receiving channel having two lateral legs at said upper portion of said receiver member and forming an opening leading to said axial bore; said axial bore near said lower portion of said receiver member including an inwardly conical tapered surface; said conical surface having a diameter larger than said shaft of said screw member and a diameter smaller than said head of said screw member; said pressure cap having upper and lower ends, said upper end comprising a concave radial portion and said lower end comprising a spherical portion;

inserting said screw member into said bore of said receiver member and positioning said screw member toward said lower portion of said receiver member such that said conical surface of said bore forms a support upon which said spherical undersurface of said head of said screw member rests upon said conical surface and said shaft of said screw member extends from said receiver member;

inserting said pressure cap into said bore of said receiver member and positioning said spherical portion of said cap upon said conical tapered recess of said head of said screw member, and aligning said concave radial portion of said cap with said u-shaped channel such that said concave radial portion is ready to receive the rod;

screwing said screw member into the spinal column of a patient;

positioning the rod upon said concave radial portion of said cap; and securing the rod within said u-shaped channel of said receiver member using a locking device; said locking device being positioned within said opening and said bore near said upper portion of said receiver member.

19. The method of claim 18 wherein said head and said shaft of said screw member comprise threaded portions.

20. The method of claim 19 wherein said conical tapered recess of said head of said screw member comprising an aperture coaxial to said shaft and designed to engage a fastening device; said cap further comprising an axial bore extending from said upper through said lower ends of said cap, said bore of said cap corresponding to said aperture of said head of said screw member allowing access for said fastening device.

21. The method of claim 20 wherein said screw member is screwed into the spinal column using said fastening device.

22. The method of claim 20 wherein said aperture of said head of said screw member is hexagon shaped and said fastening device is a hexagon socket screw key.

23. The method of claim 18 wherein said pressure cap is locked within said bore of said receiver member prior to said screw member being screwed into the spinal column.

24. The method of claim 23 wherein said receiver member further comprising a rectangular key-locking segment and a cylindrical undercut situated adjacent to said bore; said pressure cap further comprising a cylindrical undercut and a retaining ring; said key-locking segment and said undercut of said receiver member being designed to engage said undercut and said ring of said cap to form an anti-rotation and locking mechanism.

25. The method of claim 18 wherein said axial bore of said receiver member further comprises a threaded portion and said locking device further comprises a corresponding threaded portion.

26. The method of claim 25 wherein said locking device is a set screw.

27. The method of claim 25 wherein said locking device is a top locking nut.

28. The method of claim 18 wherein said legs of said u-shaped channel of said receiver member comprises a plurality of slots descending down said bore and said locking device comprising at least one protrusion designed to engage at least one of said slots of said legs of said u-shaped channel of said receiver member to secure said locking device within said receiver member.

29. The method of claim 18 wherein said locking device comprises a top and bottom portion, said bottom portion having a convex recess designed for contacting the curvature of the rod.

30. The method of claim 29 wherein said convex recess of said locking device is aligned with the curvature of the rod before locking said locking device within said receiver member.

* * * * *